United States Patent [19]

Gubbels et al.

[11] 4,005,088
[45] Jan. 25, 1977

[54] PROCESS FOR THE CHEMICAL SEPARATION OF RACEMIC MODIFICATIONS OF α-AMINOCARBOXYLIC ACID DERIVATIVES, AND CINCHONIDINE SALT INTERMEDIATES

[75] Inventors: Jan M. H. Gubbels, Venlo; Johannes P. M. Houbiers, Tegelen, both of Netherlands

[73] Assignee: Andeno B.V., Venlo, Netherlands

[22] Filed: Oct. 30, 1973

[21] Appl. No.: 410,990

[30] Foreign Application Priority Data

Nov. 11, 1972 Luxembourg .................. 66433

[52] U.S. Cl. .................. 260/284; 260/477; 260/479 R; 260/519
[51] Int. Cl.² .................. C07C 99/12
[58] Field of Search ............ 260/471 C, 519, 284, 260/479 S, 463, 479 R, 477

[56] References Cited

UNITED STATES PATENTS 3,683,015  8/1972  Dyson ........................ 260/284 X
3,794,655  2/1974  Schubel et al. ............... 260/519
3,796,748  3/1974  Holdrege ..................... 260/519 X
3,860,631  1/1975  Gleason et al. ............... 260/519 X
3,869,505  3/1975  Palmer ....................... 260/519 X

OTHER PUBLICATIONS

Cordes, Dissertation for Doctor of Philosophy at Polytechnic Institute of Brooklyn, June, 1970, University Microfilms, 313 N. First St., Ann Arbor, Michigan.
Greenstein et al., Chemistry of the Amino Acids, vol. 1, John Wiley & Sons, Inc., New York (1961) pp. 718 and 719.

Primary Examiner—Richard L. Raymond
Attorney, Agent, or Firm—Albert C. Johnston

[57] ABSTRACT

Racemic Modifications of α-aminocarboxylic acid derivatives, such as of α-amino-4-hydroxyphenylacetic acid derivatives, are prepared reliably and more economically than in known processes by reacting the DL-form of the derivative in a solvent with cinchonidine, isolating the precipitated cinchonidine salt and hydrolyzing said salt.

16 Claims, No Drawings

PROCESS FOR THE CHEMICAL SEPARATION OF RACEMIC MODIFICATIONS OF α-AMINOCARBOXYLIC ACID DERIVATIVES, AND CINCHONIDINE SALT INTERMEDIATES

The invention relates to a process for the chemical separation of racemic modifications of, possibly substituted, α-aminocarboxylic acid derviatives, and to products obtained by this process. In particular, the invention relates to a process for the chemical separation of racemic modifications of, possibly subsituted, α-amino-4-hydroxyphenylacetic acid derivatives.

At present, α-amino-4-hydroxyphenylacetic acid and its derivatives are important intermediates for the preparation of synthetic penicillins. Of the two existing optically active isomers the D(—)isomer is preferred because of its higher pharmaceutical effect in the synthetic penicillin compound. Consequently, the preparation of DL-α-amino-4-hydroxyphenylacetic acid and its resolution into optical antipodes has aroused a great amount of interest.

Processes for preparing DL-α-amino-4-hydroxyphenylacetic acid and the derivatives thereof as well as their resolution into optical antipodes are known.

The British Patent Specification No. 1,240,687 describes the preparation of DL- α -amino-4-methoxyphenylacetic acid, which is converted into DL- α -chloroacetylamino-4-methoxyphenylacetic acid with the aid of $ClCH_2.CO_2.CO.CH_2Cl$. By treating this product with acylase isolated from Hog Kidneys the L-form is selectively deacetylated. The remaining D(-)- α - chloroacetylamino-4-methoxyphenylacetic acid is then separated. The chloroacetyl group is cleaved off with boiling 2N HCl and, subsequently, the D(—)- α -amino-4-methoxyphenylacetic acid is isolated. By treating with a 48% HBr solution this acid is demethylated to give D(-)- α -amino-4-hydroxyphenylacetic acid.

Both the British Patent Specification 1,241,844 and the German "Offenlegungsschrift" 2,025,819 describe a chemical resolution into optical antipodes using quinine trihydrate. Started is with DL- α -benzyloxycarbonylamino-4-hydroxyphenylacetic acid which is treated, in boiling ethanol, with quinine trihydrate. Upon cooling, crystals of the quinine salt of the laevorotatory acid separate out. The free, laevo-rotatory D(-)-α-benzyloxycarbonylamino-4-hydroxyphenylacetic acid is obtained by treatment of the quinine salt with dilute NaOH, separation of liberated quinine by extracting it with ether and acidification of the aqueous solution. The D(-)-α-amino-4-hydroxyphenylacetic acid is obtained after catalytic hydrogenation.

The Belgian Patent Specification No. 772,894 mentions a resolution into optical antipodes using dehydroabietylamine. According to the process of this patent specification use is made of an N-acyl and/or an N,O-diacyl derivative of DL- α -amino-4-hydroxyphenylacetic acid, in order to obtain a resolution into optical antipodes of the salt formed by means of dehydroabietylamine. The N,O-diacetyl derivatives are preferred. After the salt has been resolved and the D(—)-α -acetylamino-4-acetoxyphenylacetic acid, in order to deacetylate it, is boiled with 6N HCl, there is obtained the pure D(-)-α-amino-4-hydroxyphenylacetic acid.

Biochem. J. 121 (3), pages 425 to 430 (1971) describes the separation of DL- α -amino-4-hydroxyphenylacetic acid with the aid of bromocamphorsulphonic acid.

However, each of the foregoing resolution methods has certain drawbacks. The first mentioned is disadvantageous in that it is a very difficult and time-wasting affair to isolate from Hog Kidneys acylase to the high degree of purity required. Moreover, the yield is low. Hence, acylase is a very expensive product. In addition, it is consumed during resolution and subsequent purification steps of the acetylaminocarboxylic acid. Thus, due to the above difficulties in obtaining pure acylase and its being consumed the resolution is hardly practicable from a technical point of view and, economically, it is not interesting either. The second method is disadvantageous in that quinine trihydrate is not effective, if the amine group is substituted with a radical other than a benzyloxycarbonyl radical, e.g. with an acetyl radical. So, quinine trihydrate can only be used selectively, not generally.

The separation with dehydroabietylamine according to the Belgian Patent Specification No. 772,894 is disadvantageous in that, dependent on the substituent bonded to the oxygen atom, the desired salt will now precipitate, now remain in a dissolved state.

Finally, bromocamphorsulphonic acid is disadvantageous in that it is very costly.

The object of the invention is to provide a process for the chemical separation of racemic modifications of, possibly substituted, α-aminocarboxylic acid derivatives and, in particular, of α-amino-4-hydroxyphenylacetic acid derivatives not having the drawbacks referred to before.

The process according to the invention utilizes cinchonidine as a separating agent for chemically separating racemic modifications of said derivatives.

The invention therefore relates to a process for the chemical separation of racemic modifications of, possibly substituted, α-aminocarboxylic acid derivatives, which process comprises reacting the DL-form, contained in a solvent, with cinchonidine, isolating the precipitated cinchonidine salt from the solution, and liberating the D(—)- α -aminocarboxylic acid from said salt by hydrolysis.

In particular, the invention relates to a process for the chemical separation of, possibly substituted, DL- α -aminophenylacetic acid derivatives.

Apart from the fact that the separation wtih cinchonidine proceeds readily and a fair yield of optically pure product is obtained, the use of this inexpensive product offers the following additional advantages:

1. It is effective, at least within certain bounds, irrespective of the substituents R and R', which may contain the oxygen and/or nitrogen atom of the α-aminocarboxylic acid (Formula I).

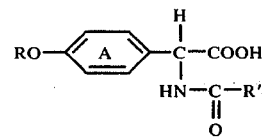

2. Irrespective of the substituents R and R' - again within certan bounds- the desired D-acid always crystallizes out as the cinchonidine salt, whereas the L-acid remains in a dissolved state.

"Irrespective of the substituents, at least within certain bounds" means that cinchonidine is not only effective, as is quinine trihydrate or dehydroabietylamine, if R stands for a methyl radical, but that R and R' may be the substituents commonly occurring in case a resolution into optical antipodes is desired. The R symbol may stand, e.g., for a hydrogen atom or an acyl, alkyl, or aralkyl radical, and the R' symbol may represent a hydrogen atom or an alkyl or aryl radical. The acyl radical may be an aliphatic or an aromatic one. The alkyl radical may, of course, be branched. In addition, the phenyl nucleus A in formula I may carry one or more of the usual substituents, such as alkyl, alkoxy, amino, halogen, etc. If the phenyl nucleus A is substituted the preferred substituents are one or two halogen atoms, particularly chlorine atoms, which then prefer to occupy the ortho position relative to the —OR group.

Preferably, the alkyl radical contains 1 up to 4, the aryl radical, up to 10, and the aralkyl radical up to 11 C-atoms. In particular, R is either a hydrogen atom or a methyl or an acetyl radical, and R' is either a hydrogen atom or a methyl radical.

The solvents preferably applied are water, particularly if R represents a hydrogen atom or an acetyl radical, and chloroform, in particular if R is a methyl radical. The amounts of cinchonidine applied in the examples hereinafter referred to may also be reduced, and the balance be completed with another base, which makes it possible to further cheapen the carrying out of the process. For, half of the DL-aminocarboxylic acid consists in fact of D- and the rest of L-acid, and cinchonidine only effects a precipitation with the D-isomer, while the cinchonidine salt of the L-isomer remains in a dissolved state. So, only that amount of cinchonidine is needed to precipitate the D-isomer completely, while half of the cinchonidine, remaining with the L-isomer in a dissolved state, may be replaced by another less expensive base such as triethylamine, sodium hydroxide, morpholine, or a compound containing ammonia, such as ammonium hydroxide. So, the molar ratio of cinchonidine to the DL- $\alpha$ -aminocarboxylic acid derivative may be between 0.2 and 1.5 to 1 and, preferably, it is within the 0.4 – 0.6 range to 1.

The invention may be clarified with the aid of the following examples.

The optical rotation was measured at a wave length of 578 and 546 millimicrons using a Zeiss light-electric 0.005° precision polarimeter. To calculate the rotation at a wave length of 589 millimicrons $\alpha_D$ use is made of the formula contained in the instruction manual for this instrument:

$$\alpha_D = \frac{\frac{\alpha_{578}}{\alpha_{546} - \alpha_{578}}}{\frac{\alpha_{578}}{\alpha_{546} - \alpha_{578}} + 1.3727} \times \alpha_{546}$$

The indication $c = 1$, parenthesized behind the optical rotations measured, means that the concentration of the acid amounted to 1g per 100 ml solution.

EXAMPLE 1 a. Preparation of DL- $\alpha$ -acetylamino-4-methoxyphenylacetic acid from DL- $\alpha$-amino-4-methoxyphenylacetic acid.

To a solution containing 181 g (1.0 mole) of DL- $\alpha$ -amino-4-methoxyphenylacetic acid and 80 g (2.0 moles) of sodium hydroxide in 1 l of water was added 153 g (1.5 moles) of acetic anhydride at room temperature. This mixture was stirred for half an hour and then, adding conc. hydrochloric acid, brought to pH 1. The precipitate filtered off and dried, the yield was 208 g (= 0.93 mole = 93%) of DL- $\alpha$ -acetylamino-4-methoxyphenylacetic acid I.

b. Isolation of D(—)- $\alpha$ -acetylamino-4-methoxyphenylacetic acid from DL- $\alpha$ -acetylamino-4-methoxyphenylacetic acid I While heating, 54 g (0.185 mole) of cinchonidine (grade purum, manufactured by Fluka AG) and 34 g (0.152 mole) of the acid I were dissolved in 600 ml of chloroform. Some crystal nuclei were introduced and the mixture was stirred at room temperature for approximately 12 hours. The cinchonidine salt was filtered off and washed twice with 100 ml of chloroform. After drying at reduced pressure the yield of salt was 35 g. In addition to the D(—)- $\alpha$ -acetylamino-4-methoxyphenylacetic acid II the salt thus obtained also contained cinchonidine and chloroform in a molar ratio of 1 : 1 : 1. Thus, these 35 g of salt corresponded to 0.055 mole of acid II (= a yield of 72.5%). The specific rotation of this salt was $[\alpha]_{546} = -142°$ and $[\alpha]_{578} = -123°$, respectively ($c = 1$ in methanol at room temperature). The resulting $[\alpha]_D$ value proved to be $-117°$. To isolate the pure acid II, 24 g of the salt obtained above were shaken with 100 ml of water, 12 ml of conc. ammonium hydroxide and 70 ml. of chloroform. The chloroform layer was separated and the extracting process was repeated, once with 70 ml of chloroform and once with 100 ml of ether. The aqueous layer was adjusted to pH 1 by the addition of conc. hydrochloric acid; the precipitated acid was filtered off and washed. After drying, the yield was 7.6 g, i.e. 74% pure D(—)- $\alpha$ -acetylamino-4-methoxyphenylacetic acid II. The specific rotation amounted to $[\alpha]_{546} = -255.3°$ and $[\alpha]_{578} = -221°$, respectively. ($c = 1$,methanol).

Instead of chloroform dioxane may be used. In that case, however, the resulting product has to be recrystallized more frequently, which generally leads to a lower yield.

c. Conversion of the D(—)- $\alpha$ -acetylamino-4-methoxyphenylacetic acid II into D(—)- $\alpha$ -amino-4-methoxyphenylacetic acid.

A mixture consisting of 6.5 g of the acid II, 8 ml of conc. hydrochloric acid and 38 ml of water was refluxed for 3 hours. After cooling, the mixture was adjusted to pH 5.5 by the addition of ammonium hydroxide, the acid precipitating. The precipitate was filtered off, washed with a little water, and dried. The yield was 5.0 g = 95% of D(—)- $\alpha$ -amino-4-methoxyphenylacetic acid III. The specific rotation amounted to $[\alpha]_{546} = -190°$ and $[\alpha]_{578} = -164°$, respectively ($c = 1$, 1N HCl).

The resulting $[\alpha]_D$ proved to be $-156°$, whereas the highest value known in literature is the value mentioned in the British Patent Specification No. 1,240,687, viz. $[\alpha]_D^{25} = 150.4°$ ($c = 1$, 1N HCl).

d. Conversion of the D(—)- $\alpha$ -amino-4-methoxyphenylacetic acid III into D(—)- $\alpha$ -amino-4-hydroxyphenylacetic acid Demethylation of the acid III to D(—)- $\alpha$ -amino-4-hydroxyphenylacetic acid IV occurred as described on page 6, lines 6 to 32, of the British Patent Specification 1,240,687. The results obtained were identical to those indicated in said patent.

EXAMPLE 2 a. Preparation of DL-α-acetylamino-4-acetoxyphenylacetic acid from DL-α-amino-4-hydroxyphenylacetic acid 167 g (1.0 mole) of DL-α-amino-4-hydroxyphenylacetic acid and 160 g (4.0 moles) of NaOH were dissolved in one liter of water and to that solution were added 250 g (2.5 moles) of acetic anhydride at room temperature. The mixture was stirred for half an hour and, subsequently, conc. hydrochloric acid was added to such an amount that the mixture had a pH 1 value.

Filtered off and dried, the yield was 235 g = 93.5% of DL-α-acetylamino-4-acetoxyphenylacetic acid V.

b. Preparation of the cinchonidine salt of D(-31)-α-acetylamino-4-acetoxyphenylacetic acid from the DL-α-acetylamino-4-acetoxyphenylacetic acid V 100 g (0.40 mole) of the acid V and 120 g (0.41 mole) of cinchonidine were dissolved in 800 ml of boiling water. While stirring, the mixture was cooled to 76° C after which crystal nuclei were introduced to the clear solution. The mixture was stirred again for 16 hours and the precipitate filtered off at room temperature. The salt was washed with water and recrystallized again, using water as a solvent. After filtering off and washing, the yield of D(−)-α-acetylamino-4-acetoxyphenylacetic acid.cinchonidine salt VI was 63 g (= 58%).

The specific rotation of this salt was $[\alpha]_{546} = -173,4°$ and $[\alpha]_{578} = -150.2°$, respectively (c = 1,methanol), from which a $[\alpha]_D$ value of −143° could be calculated.

The use of dichloroethane or dioxane, instead of water, yields the same result but in that case the resulting product has to be crystallized frequently.

c. Conversion the cinchonidine salt VI into the D(-31)-α-amino-4-hydroxyphenylacetic acid IV 63 g (0.115 mole) of the salt VI were shaken with 35 ml of conc. ammonium hydroxide, 100 ml of water and 250 ml of chloroform, after which the chloroform layer was separated. The aqueous layer was extracted again, viz. twice with 75 ml portions of chloroform and once with 100 ml of ether. After the addition of 100 ml of conc. hydrochloric acid the mixture was refluxed for three hours. The excess of hydrochloric acid was removed under reduced pressure, the residue absorbed in water, and the mixture was brought to a pH 6 value by adding ammonium hydroxide at a temperature of 55° C. The precipitated amino-acid was isolated and washed with a little water. After drying, the yield was 11.0 g = 57% of D(−)-α-amino-4-hydroxyphenylacetic acid IV. The specific rotation of this acid was $[\alpha]_{546} = -190.4°$ and $[\alpha]_{578} = -164.7°$, respectively (c = 1, 1N HCl). The $[\alpha]_D$ value was calculated to be 157°.

EXAMPLE 3 a. Preparation of DL-α-acetylamino-4-hydroxyphenylacetic acid from the DL-α-acetylamino-4-acetoxyphenylacetic acid V By adding a 45 percent solution of sodium hydroxide the suspension of 120 g (0.475 mole) of acid V in 500 ml of water was brought to a pH 12.5 value. After two hours' stirring at room temperature the mixture was acidified to a pH 3 value. After 100 g of NaCl had been added the precipitate formed was filtered off and washed with a little cold water. After drying, the yield was 93 g, i.e. 94% of DL-α-acetylamino-4-hydroxyphenylacetic acid VII.

b. Preparation of the cinchonidine salt of D(−)-α-acetylamino-4-hydroxyphenylacetic acid from the DL-α-acetylamino-4-hydroxyphenylacetic acid VII A mixture containing 78 g (0.374 mole) of the acid VII, 113 g (0.384 mole) of cinchonidine and 750 ml of water was heated to boiling point, after which it was cooled to room temperature in the current of 24 hours. The cinchonidine salt VIII was filtered off and recrystallized twice, using water as a solvent. After drying, the yield of salt VIII was 46.5 g (50%). The specific rotation measured amounted to $[\alpha]_{546} = -178°$ and $[\alpha]_{578} = -154°$, respectively (c = 1,methanol). Instead of water, isopropyl alcohol may be used as a solvent.

c. Preparation of D(−)-α-amino-4-hydroxyphenylacetic acid IV from the cinchonidine salt VIII of D(−)-α-acetylamino-4-hydroxyphenylacetic acid.

34 g (0.68 mole) of the salt VIII was hydrolysed in the way, as described for the salt VI in example 2 (c). The yield was 8.0 g = 71% of the amino-acid IV.

The specific rotation was $[\alpha]_{546} = -190.6°$ and $[\alpha]_{578} = -165°$, respectively (c = 1, 1N HCl), resulting in a $[\alpha]_D$ value of <157°.

EXAMPLE 4

The Example 2 was repeated, it being understood that a mixture of cinchonidine and ammonium hydroxide was employed, instead of cinchonidine only.

100 g (0.40 mole) of the acid V, see Example 2 (a), e.g., 70.6 g (0.24 mole) of cinchonidine, and 12.3 ml of 13N ammonium hydroxide (0.16 mole) were dissolved in 800 ml of boiling water and subjected to purification procedures, as described in Example 2 (b).

The yield amounted to approximately 60% D(−)-α-acetylamino-4-acetoxyphenylacetic acid.cinchonidines salt VI, and the $[\alpha]_D$ value was −136°.

The conversion of the salt VI into D(−)-α-amino-4-hydroxyphenylacetic acid was brought about according to the Example 2 (c), the results obtained being the same.

Example 5

Proceeded was in the way as described in Example 4 but instead of the amounts referred to above were used 47.2 g (0.16 mole) of cinchonidine and 18.5 ml 13N of ammonium hydroxide (0.24 mole). The same results were obtained.

What we claim is:

1. Cinchonidine salt of a D-antipode of an α-aminocarboxylic acid of the formula

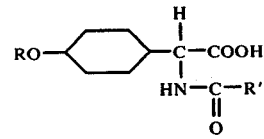

wherein R is either a hydrogen atom or a methyl or an acetyl radical, and R' stands for a hydrogen atom or a methyl radical.

2. A process for the chemical separation of racemic modifications of, possibly substituted, α-aminocarboxylic acid derivatives, which process comprises reacting a N-acylated DL-form of an α-aminophenylacetic acid in a solvent, at a temperature in the range from about room temperature to the boiling point of the solvent, with cinchonidine in an amount sufficient at least to form a cinchonidine salt with the amount of D-antipode contained in said acylated DL-form, said reacting being effected for a period of hours, and with cooling of the reaction mixture if it was heated, sufficient to cause the formation of a crystalline precipitate containing a cinchonidine salt of said D-antipode, and selectively isolating said salt from said precipitate; said DL-form being a compound of the formula

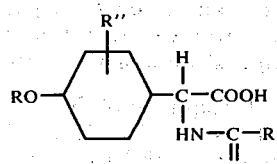

in which R is a hydrogen atom, an acyl group, an alkyl group having 1 to 4 carbon atoms or an aralkyl group having up to 11 carbon atoms, R' is a hydrogen atom or an alkyl group having 1 to 4 carbon atoms or an aryl radical having up to 10 carbon atoms, and R" stands for hydrogen or hydrogen and one or two halogen atoms.

3. Process as claimed in claim 2, wherein R is a hydrogen atom or a methyl or an acetyl radical, and R' is a hydrogen atom or a methyl radical.

4. Process as claimed in claim 2, wherein said solvent is water or chloroform.

5. Process as claimed in claim 2, wherein in said reacting the molar ratio of cinchonidine to said acylated DL-form is between 0.2 and 1.5 to 1.

6. Process according to claim 5, wherein said molar ratio is within the 0.4 – 0.6 range to 1.

7. A process according to claim 2, which further comprises hydrolyzing said cinchonidine salt in an alkaline aqueous medium, extracting the cinchonidine from said aqueous medium and acidifying the residual alkaline solution to precipitate said D-antipode, and then de-acylating said D-antipode in an acid solution and neutralizing said acid solution to precipitate the D-isomer of said compound.

8. A process according to claim 2, said reacting being effected in the presence of ammonium hydroxide in a quantity sufficient to react with the L-antipode of said acylated DL-form, the amount of said cinchonidine being in a molar ratio of between about 0.4 and 0.6 to the amount of said acylated DL-form.

9. A process according to claim 2, said reacting being effected by heating the reaction mixture, said solvent being selected from the group consisting of water, chloroform, dioxane and dichloroethane, said crystallizing being effected by cooling the reaction mixture and stirring it for a period of hours.

10. A process according to claim 2, wherein R is a hydrogen atom or an acetyl radical and said solvent is water, said reacting being effected by boiling the reaction mixture, said crystallizing being effected by cooling the reaction mixture and stirring it for a period of hours.

11. A process according to claim 2, wherein R is a methyl radical and said solvent is chloroform, said reacting being effected by heating the reaction mixture, said crystallizing being effected by cooling the reaction mixture and stirring it for a period of hours.

12. A process for preparing the D-isomer of an α-aminocarboxylic acid compound, which process comprises reacting a N-acylated DL-form of an α-aminophenylacetic acid with cinchonidine in an amount equivalent to between 0.2 and 1.5 mols of cinchonidine per mol of said acylated DL-form by heating the reactants in a solvent selected from the group consisting of water, chloroform, dioxane and dichloroethane to a temperature not exceeding the boiling point of the solvent used; cooling the reaction mixture and stirring it for a period of hours sufficient for selectively crystallizing from it a precipitate containing the cinchonidine salt of the D-antipode contained in said acylated DL-form; isolating said salt; then hydrolyzing said salt in an alkaline aqueous medium, extracting cinchonidine from the aqueous medium and acidifying the residual alkaline solution to precipitate said D-antipode; and then de-acylating said D-antipode in an acid solution and neutralizing said acid solution to precipitate the D-isomer of said compound, said DL-form being of a compound of the formula

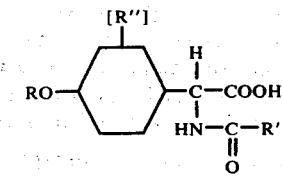

in which R is a hydrogen atom, an acyl group, an alkyl group having 1 to 4 carbon atoms or an aralkyl group having up to 11 carbon atoms and R' is a hydrogen atom or an alkyl group having 1 to 4 carbon atoms or an aryl radical containing up to 10 carbon atoms.

13. A process according to claim 2, said reacting with cinchonidine being effected in the presence of at least one other base that forms with the L-antipode of said DL-form salt that remains dissolved in said solvent.

14. A process according to claim 13, said at least one other base being selected from the group consisting of triethylamine, sodium hydroxide, morpholine and ammonium compounds.

15. A process according to claim 12, said reacting with cinchonidine being effected in the presence of at least one other base that forms with the L-antipode of said DL-form salt that remains dissolved in said solvent.

16. A process according to claim 15, said at least one other base being selected from the group consisting of triethylamine, sodium hydroxide, morpholine and ammonium compounds.

* * * * *